United States Patent
Bokil

(10) Patent No.: US 10,265,531 B2
(45) Date of Patent: Apr. 23, 2019

(54) DETECTION OF LEAD ORIENTATION

(71) Applicant: Boston Scientific Neuromodulation Corporation, Valencia, CA (US)

(72) Inventor: Hemant Bokil, Santa Monica, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 253 days.

(21) Appl. No.: 15/252,438

(22) Filed: Aug. 31, 2016

(65) Prior Publication Data

US 2017/0056678 A1 Mar. 2, 2017

Related U.S. Application Data

(60) Provisional application No. 62/212,775, filed on Sep. 1, 2015.

(51) Int. Cl.
| | |
|---|---|
| *A61N 1/372* | (2006.01) |
| *A61B 6/12* | (2006.01) |
| *A61N 1/36* | (2006.01) |
| *A61N 1/05* | (2006.01) |
| *G06T 7/73* | (2017.01) |

(Continued)

(52) U.S. Cl.
CPC ............ *A61N 1/37217* (2013.01); *A61B 6/12* (2013.01); *A61N 1/0534* (2013.01); *A61N 1/3605* (2013.01); *A61N 1/37247* (2013.01); *G06T 7/74* (2017.01); *A61B 6/032* (2013.01); *A61B 2090/3966* (2016.02); *A61N 1/05* (2013.01);

(Continued)

(58) Field of Classification Search
CPC .............. A61N 1/37217; A61N 1/0534; A61N 1/3605; A61N 1/37247; A61N 1/05; G06T 7/74; G06T 7/73; G06T 2207/10081; G06T 7/0012; A61B 6/12; A61B 2090/3966; A61B 6/032
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |

(Continued)

OTHER PUBLICATIONS

U.S. Appl. No. 15/729,424, filed Oct. 10, 2017.

(Continued)

*Primary Examiner* — Rex R Holmes
(74) *Attorney, Agent, or Firm* — Lowe Graham Jones PLLC; Bruce E. Black

(57) ABSTRACT

Systems and methods for determining a rotational orientation of a lead for use in electrostimulation of a body tissue are disclosed. A system may receive image data of at least a portion of the lead including image data of a marker configured to identify a rotational orientation of the lead. The system may receive at least one template of the lead having a specified rotational orientation. Each template may include a reference data cube and a reference marker direction vector. The system may generate a target data cube of the marker using the image data of the marker, and register the reference data cube to the target data cube to produce a transformation operator. The system may estimate the rotational orientation of the lead using the reference marker direction vector and the determined transformation operator.

20 Claims, 10 Drawing Sheets

(51) Int. Cl.
*A61B 6/03* (2006.01)
*A61B 90/00* (2016.01)

(52) U.S. Cl.
CPC .............. *G06T 2207/10072* (2013.01); *G06T 2207/30021* (2013.01)

(56) References Cited

U.S. PATENT DOCUMENTS

| | | |
|---|---|---|
| 6,609,029 B1 | 8/2003 | Mann et al. |
| 6,609,032 B1 | 8/2003 | Woods et al. |
| 6,741,892 B1 | 8/2004 | Meadows et al. |
| 6,895,280 B2 | 5/2005 | Meadows et al. |
| 7,244,150 B1 | 7/2007 | Brase et al. |
| 7,437,193 B2 | 10/2008 | Parramon et al. |
| 7,450,997 B1 | 11/2008 | Pianca et al. |
| 7,650,184 B2 | 1/2010 | Walter |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 8,019,439 B2 | 9/2011 | Kuzma et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,326,433 B2 | 12/2012 | Blum et al. |
| 8,364,278 B2 | 1/2013 | Pianca et al. |
| 8,391,985 B2 | 3/2013 | McDonald |
| 8,473,061 B2 | 6/2013 | Moffitt et al. |
| 8,571,665 B2 | 10/2013 | Moffitt et al. |
| 8,675,945 B2 | 3/2014 | Barnhorst et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,849,632 B2 | 9/2014 | Sparks et al. |
| 8,875,391 B2 | 11/2014 | Pianca |
| 8,958,615 B2 | 2/2015 | Blum et al. |
| 9,037,256 B2 | 5/2015 | Bokil et al. |
| 2007/0150036 A1 | 6/2007 | Anderson |
| 2009/0187222 A1 | 7/2009 | Barker |
| 2009/0204192 A1 | 8/2009 | Carlton et al. |
| 2009/0276021 A1 | 11/2009 | Meadows et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2010/0030298 A1 | 2/2010 | Martens et al. |
| 2010/0049276 A1* | 2/2010 | Blum ................ G16H 50/50 607/45 |
| 2010/0076535 A1 | 3/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0257707 A1 | 10/2011 | Kothandaraman |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0046715 A1 | 2/2012 | Moffitt et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0314919 A1 | 12/2012 | Sparks et al. |
| 2012/0314924 A1 | 12/2012 | Carlton et al. |
| 2012/0316615 A1 | 12/2012 | DiGiore et al. |
| 2013/0039550 A1* | 2/2013 | Blum .................. G06T 7/0014 382/128 |
| 2013/0105071 A1 | 5/2013 | DiGiore et al. |
| 2013/0116744 A1 | 5/2013 | Blum et al. |
| 2013/0197424 A1 | 8/2013 | Bedenbaugh |
| 2013/0197602 A1 | 8/2013 | Pianca et al. |
| 2013/0267837 A1 | 10/2013 | Schulte et al. |
| 2014/0039587 A1 | 2/2014 | Romero |
| 2014/0122379 A1 | 5/2014 | Moffitt et al. |
| 2014/0228470 A1 | 8/2014 | Howard |
| 2014/0257428 A1 | 9/2014 | Zhu |
| 2014/0276002 A1* | 9/2014 | West ................... A61B 5/061 600/424 |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2014/0371819 A1 | 12/2014 | Goetz et al. |
| 2015/0018915 A1 | 1/2015 | Leven |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0151113 A1 | 6/2015 | Govea et al. |
| 2015/0157851 A1 | 6/2015 | Sefkow et al. |
| 2016/0030749 A1 | 2/2016 | Carcieri et al. |
| 2016/0228692 A1 | 8/2016 | Steinke et al. |
| 2017/0056678 A1 | 3/2017 | Bokil |
| 2017/0061627 A1 | 3/2017 | Bokil |

OTHER PUBLICATIONS

U.S. Appl. No. 15/783,807, filed Oct. 13, 2017.
International Search Report and Written Opinion for PCT Application No. PCT/US2016/049565 dated Jan. 11, 2017.

* cited by examiner

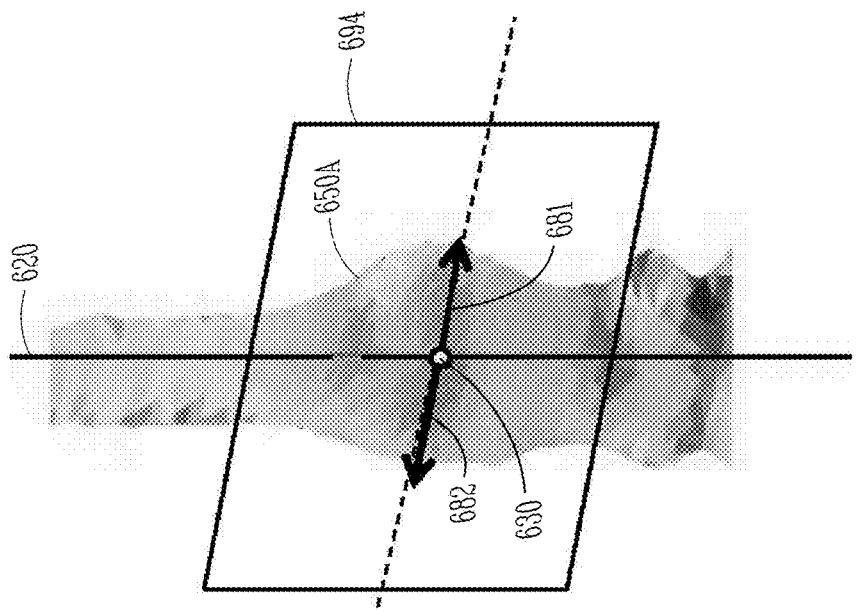
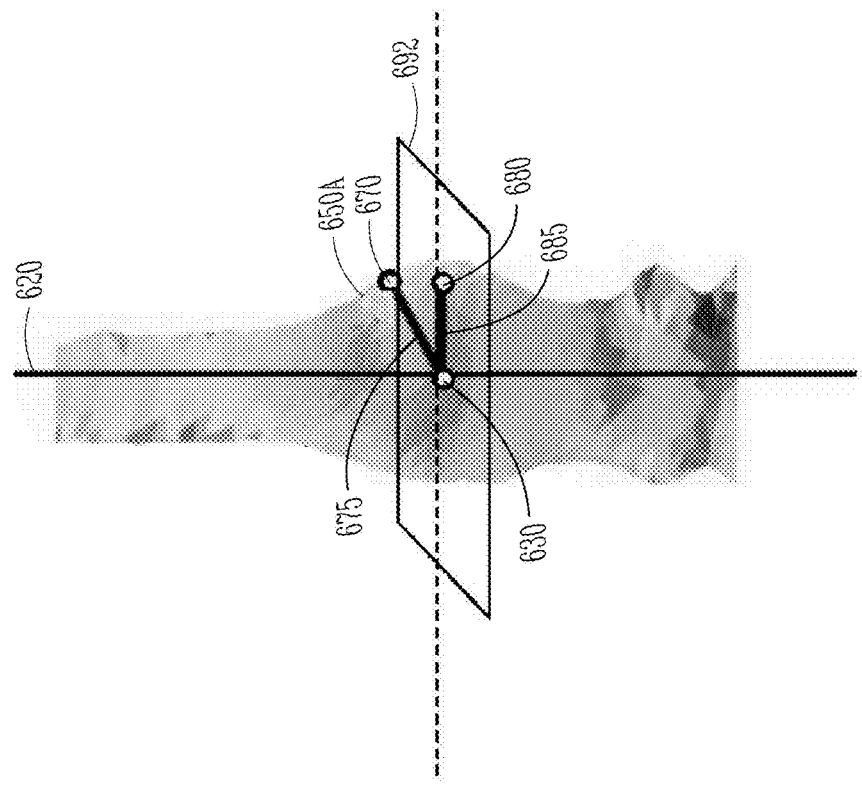
Fig. 6D
Fig. 6C ized lead position and/or orientation may also reduce energy consumption and thereby extending longevity of the implantable neuromodulator.

DETECTION OF LEAD ORIENTATION

CLAIM OF PRIORITY

This application claims the benefit of priority under 35 U.S.C. § 119(e) of U.S. Provisional Patent Application Ser. No. 62/212,775, filed on Sep. 1, 2015, which is herein incorporated by reference in its entirety.

TECHNICAL FIELD

This document relates generally to medical devices, and more particularly, to systems, devices, and methods for detecting an orientation of a lead.

BACKGROUND

Neuromodulation, also referred to as neurostimulation, has been proposed as a therapy for a number of conditions. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neuromodulator, also referred to as an implantable pulse generator, and one or more implantable leads each including one or more electrodes. The implantable neuromodulator may deliver neuromodulation energy through one or more electrodes placed on or near a target neural tissue. An external programming device may be used to program the implantable neuromodulator with parameters controlling the delivery of the neuromodulation energy.

OVERVIEW

Efficacy and efficiency of certain neuromodulation therapies may be affected by the position and/or orientation of the implantable leads. Proper lead direction and orientation may allow the lead to be used to more accurately target tissue that is desired to be modulated while avoiding or reducing undesirable side-effects caused by unintentionally modulating neighboring cell populations next to or around the target neural structures. Additionally, an improved lead position and/or orientation may also reduce energy consumption and thereby extending longevity of the implantable neuromodulator.

Some neuromodulation systems, such as those used for DBS or SCS, may include leads that have a large number of electrodes for stimulating neural targets. In the context of DBS, a neuromodulation lead may have a complex arrangement of multiple electrodes that are not only distributed axially along the leads, but also distributed circumferentially around the lead. Such a lead, also known as a directional lead, presents a multitude of selections of stimulation parameter sets to the clinician.

Selection of the electrodes on a lead to be active and programming neuromodulation using the selected electrodes may be complicated and time consuming. Diagnostic imaging equipment may be used to localize circumferential locations of the electrodes in the operating room or during follow-up, an orientation of the lead may be determined with respect to an imaging axis of the diagnostic equipment. Conventional lead location methods may be used to identify longitudinal contacts of column electrodes (also known as ring electrodes) along the length of the lead relative to a neural target. However, such conventional lead location methods may not provide adequate information about the rotational orientation of the lead. The present subject matter effectively and efficiently determines an orientation of a lead to facilitate electrode selection and programming of the neuromodulation system.

This document discusses, among other things, an embodiment of a system for determining a rotational orientation of a lead for use in electrostimulation of a body tissue. The system may receive image data of at least a portion of the lead including image data of a marker configured to identify a rotational orientation of the lead. The system may receive at least one template of the lead having a specified rotational orientation. Each template may include a reference data cube and a reference marker direction vector. The system may generate a target data cube of the marker using the image data of the marker, and register the reference data cube to the target data cube to produce a transformation operator. The system may estimate the rotational orientation of the lead using the reference marker direction vector and the determined transformation operator.

In Example 1, a system for determining a rotational orientation of a lead for use in electrostimulation of a body tissue is disclosed. The lead can have a longitudinal lead axis and a marker configured to identify a rotational orientation about a longitudinal axis of the lead. The can comprise a data input circuit, a template receiver circuit, a lead orientation estimator circuit, and an output circuit. The data input circuit can receive image data of at least a portion of the lead including image data of the marker. The template receiver circuit can receive at least one template of the lead having a specified rotational orientation, the at least one template including a reference data cube ($X_R$) of the marker and a reference marker direction vector ($v_R$) indicative of the specified rotational orientation of the lead about the longitudinal axis. The lead orientation estimator circuit can include a marker recognition circuit that can produce a target data cube ($X_T$) of the marker using the image data of the marker, and a data registration circuit that can register the reference data cube ($X_R$) to the target data cube ($X_T$) to produce a transformation operator ($\Phi$) for transforming $X_R$ into a transformed reference data cube $\Phi(X_R)$ that matches $X_T$ within a specified margin. The estimator circuit can estimate the rotational orientation of the lead using the reference marker direction vector ($v_R$) and the determined transformation operator ($\Phi$). The output unit can produce a graphical representation of the lead and at least the estimated target marker direction vector.

Example 2 can include, or can optionally be combined with the subject matter of Example 1 to optionally include, the data input circuit that can receive the image data including data of a computed tomography (CT) scan of the marker.

Example 3 can include, or can optionally be combined with the subject matter of Example 2 to optionally include, the marker recognition circuit that can identify the marker using an anisotropic shape of the CT scan of the marker, and produce the target data cube ($X_T$) of the marker using the image data of the identified marker.

Example 4 can include, or can optionally be combined with the subject matter of Example 3 to optionally include, the marker that can include a first portion and a second portion. The first portion can include a radiopaque band around a circumference of the lead and having an anisotropic shape of a bulge under the CT scan. The second portion can define a radiolucent window having an anisotropic shape of a dimple under the CT scan.

Example 5 can include, or can optionally be combined with the subject matter of one or any combination of Examples 1 through 4 to include, a template formation circuit that can be coupled to the data input circuit. The data input circuit can receive image data of the lead obtained when the lead is substantially aligned with an imaging axis, where the image data can include image data of the marker. The template formation circuit can generate a template of the lead, which includes identify a lead tip and a lead shaft using the image data, detect a lead axis using the identified lead tip and lead shaft, identify the marker using the image data of the marker, produce the reference data cube ($X_R$) of the template using the image data of the marker and the detected lead axis, and determine the reference direction vector ($v_R$) of the template using the reference data cube.

Example 6 can include, or can optionally be combined with the subject matter of Example 5 to optionally include, a user interface that includes a display screen. The user interface can enable a user to input the reference direction vector and to display the user-inputted reference direction vector on the display screen. The template formation circuit can generate the one or more templates using the user-provided reference direction vector.

Example 7 can include, or can optionally be combined with the subject matter of Example 5 to optionally include, the template formation circuit that can determine the reference direction vector. The template formation circuit can detect a midpoint of the marker using the identified lead tip and the lead shaft, detect a bulging point within the identified marker where the bulging point is spatially farther away from the midpoint of the marker than other points within the identified marker, generate an initial marker direction vector that originates at the midpoint of the marker and points to the bulging point, and determine the reference direction vector ($v_R$) as a projection of the initial marker direction vector onto a plane perpendicular to the detected lead axis.

Example 8 can include, or can optionally be combined with the subject matter of Example 5 to optionally include, the template formation circuit that can determine the reference direction vector. The template formation circuit can identify a symmetric plane through the detected lead axis around which the image data of the marker is substantially reflective symmetric, and produce two candidate marker direction vectors along the symmetric plane, originating from and perpendicular to the lead axis, and pointing to two opposite directions. The template formation circuit can determine the reference direction vector ($v_R$) as one of the two candidate marker direction vectors that is spatially closer to a bulging point within the identified marker than the other of the two candidate marker direction vector.

Example 9 can include, or can optionally be combined with the subject matter of one or any combination of Examples 1 through 8 to include, the estimator circuit that can estimate the rotational orientation of the lead by applying the determined transformation operator ($\Phi$) to the reference direction vector ($v_R$) to produce an estimated marker direction vector ($\tilde{v}_T$) indicative of the rotational orientation of the lead relative to an imaging axis used for producing the image data of the at least a portion of the lead.

Example 10 can include, or can optionally be combined with the subject matter of one or any combination of Examples 1 through 9 to include, the transformation operator ($\Phi$) that can include a rigid transformation or an affine transformation.

Example 11 can include, or can optionally be combined with the subject matter of one or any combination of Examples 1 through 10 to include, the data registration circuit that can produce the transformation operator ($\Phi$) in response to a multi-dimensional distance measure between the transformed reference data cube $\Phi(X_R)$ and the target data cube $X_T$ falling below a specified threshold.

Example 12 can include, or can optionally be combined with the subject matter of one or any combination of Examples 1 through 11 to include, the template receiver circuit that can receive two or more templates of the lead, and the data registration circuit that can perform a multi-atlas registration of respective reference data cubes associated with the two or more templates to the target data cube.

Example 13 can include, or can optionally be combined with the subject matter of Example 12 to optionally include, the estimator circuit that can produce two or more estimated marker direction vectors of the lead by applying the respective transformation operators to the reference direction vector ($v_R$), and determine the rotational orientation of the lead using a combination of the two or more estimated marker direction vectors.

Example 14 can include, or can optionally be combined with the subject matter of Example 13 to optionally include, the estimator circuit that can produce a confidence indicator of the estimated rotational orientation of the lead using the two or more estimated marker direction vectors.

Example 15 can include, or can optionally be combined with the subject matter of one or any combination of Examples 1 through 14 to include, an electrostimulator circuit that can generate directional electrostimulation for modulating the body tissue using the lead oriented at least according to the determined rotational orientation.

In Example 16, a method for determining a rotational orientation of a lead for use in electrostimulation of a body tissue is disclosed. The lead has a longitudinal lead axis and a marker configured to identify a rotational orientation about the longitudinal axis of the lead. The method can comprise steps of receiving image data of at least a portion of the lead including image data of the marker; receiving at least one template of the lead having a specified rotational orientation, where the at least one template can include a reference data cube ($X_R$) of the marker and a reference marker direction vector ($v_R$) indicative of the specified rotational orientation of the lead about the longitudinal axis; producing a target data cube ($X_T$) of the marker using the image data of the marker; registering the reference data cube ($X_R$) to the target data cube ($X_T$) to produce a transformation operator ($\Phi$) for transforming $X_R$ into a transformed reference data cube $\Phi(X_R)$ that matches $X_T$ within a specified margin; and estimating the rotational orientation of the lead using the reference marker direction vector ($v_R$) and the determined transformation operator ($\Phi$).

Example 17 can include, or can optionally be combined with the subject matter of Example 16 to optionally include, receiving the image data that can include receiving image data of a computed tomography (CT) scan of the marker.

Example 18 can include, or can optionally be combined with the subject matter of Example 16 to optionally include, creating a template of the lead, which can include steps of receiving image data of the lead obtained when the lead is substantially aligned with an imaging axis where the image data of the lead can include image data of the marker; identifying a lead tip and a lead shaft using the image data; detecting a lead axis using the identified lead tip and lead shaft; identifying the marker using the image data; producing a reference data cube ($X_R$) of the template using the image data of the marker and the detected lead axis; and determining a reference direction vector ($v_R$) of the template using the reference data cube.

Example 19 can include, or can optionally be combined with the subject matter of Example 18 to optionally include, determining the reference direction vector that can include steps of detecting a midpoint of the marker using the identified lead tip and the lead shaft; detecting a bulging point within the identified marker and spatially farther away from the midpoint of the marker than other points within the identified marker; generating an initial marker direction vector that originates at the midpoint of the marker and points to the bulging point; and determining the reference direction vector ($v_R$) as a projection of the initial marker direction vector onto a plane perpendicular to the detected lead axis.

Example 20 can include, or can optionally be combined with the subject matter of Example 18 to optionally include, determining the reference direction vector that can include steps of identifying a symmetric plane through the detected lead axis around which the image data of the marker is substantially reflective symmetric; producing two candidate marker direction vectors, along the symmetric plane, that originate from and are perpendicular to the lead axis and point to two opposite directions; and determining the reference direction vector ($v_R$) as one of the two candidate marker direction vectors that is spatially closer to a bulging point within the identified marker than the other of the two candidate marker direction vector.

Example 21 can include, or can optionally be combined with the subject matter of Example 16 to optionally include, estimating the rotational orientation of the lead that can include applying the determined transformation operator ($\Phi$) to the reference direction vector ($v_R$) to produce an estimated marker direction vector ($\hat{v}_T$) indicative of the rotational orientation of the lead relative to an imaging axis used for producing the image data of the at least a portion of the lead.

Example 22 can include, or can optionally be combined with the subject matter of Example 16 to optionally include, registering the reference data cube ($X_R$) to the target data cube ($X_T$) that can include performing a multi-atlas registration of respective reference data cubes associated with the two or more templates to the target data cube, to produce respective transformation operators corresponding to the two or more templates, and estimating the rotational orientation of the lead that can include estimating the rotational orientation using a combination of the two or more estimated marker direction vectors estimated using reference direction vectors and respective transformation operators.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 6A-D illustrate, by way of example and not limitation, methods for forming a data cube and directional vector of a template of marker.

DETAILED DESCRIPTION

Various embodiments disclosed herein include systems, devices, and methods for determining a rotational orientation of a lead for use in electrostimulation of a body tissue. Image data of at least a portion of the lead, including image data of a marker configured to identify a rotational orientation of the lead, may be used to estimate the lead orientation. A system may receive at least one template of the lead having a specified rotational orientation. Each template may include a reference data cube and a reference marker direction vector. The system may generate a target data cube of the marker using the image data of the marker, and register the reference data cube to the target data cube to produce a spatial transformation operator. The rotational orientation of the lead may be estimated such as by applying the spatial transformation operator to the reference marker direction vector.

Figure 1:
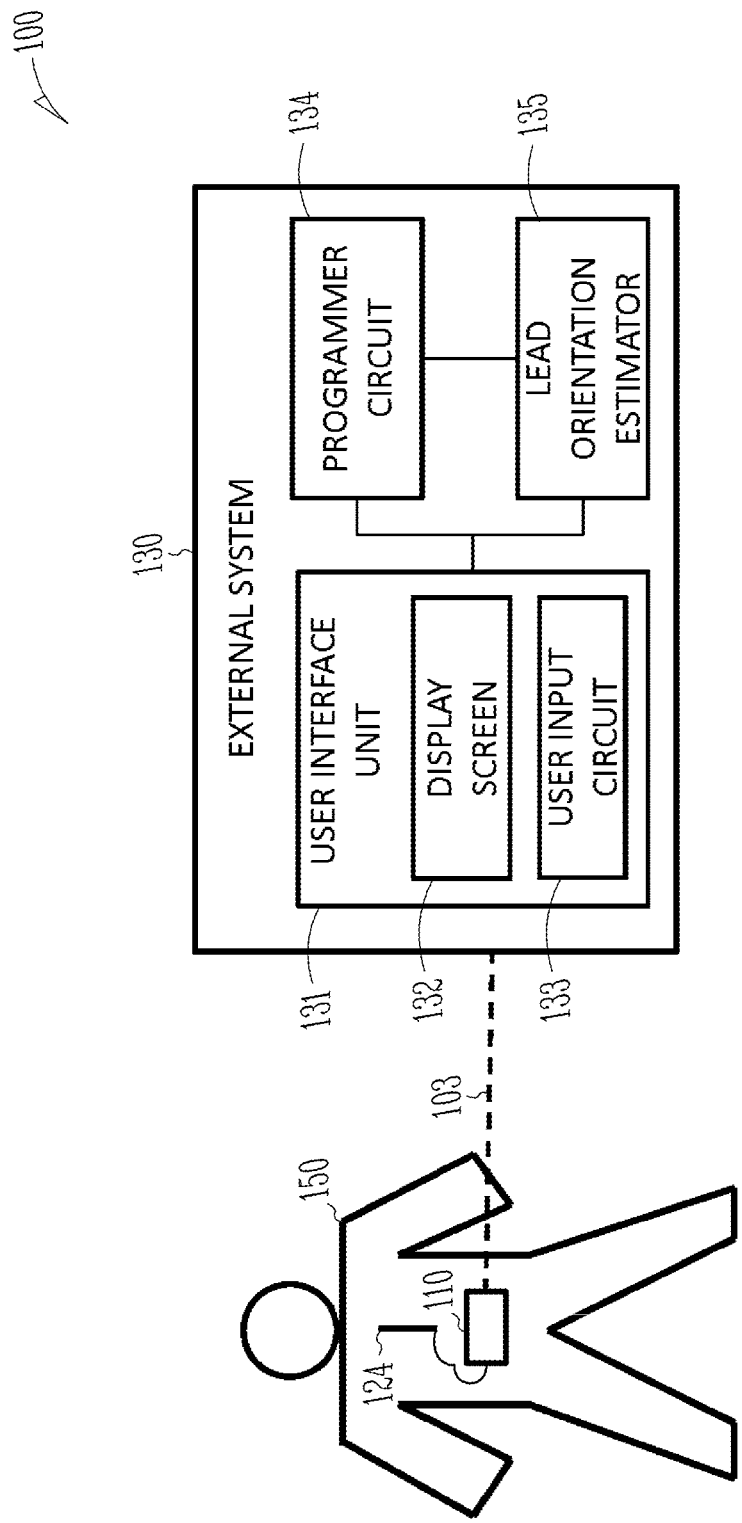
FIG. 1 illustrates, by way of example and not limitation, a neuromodulation system and portions of an environment in which the neuromodulation system operates.

FIG. 1 illustrates, by way of example and not limitation, an example of a neuromodulation system 100 and portions of an environment in which the neuromodulation system 100 may operate. The neuromodulation system 100 may include an ambulatory medical device (AMD), such as a subcutaneously implanted or a wearable electrostimulation device, associated with a subject 120 such as a patient. By way of example and not limitation, the AMD may include an implantable neuromodulator device (IND) 110. The IND 110 may generate one or more types of modifying agents for delivery to target tissues in the nervous system for medical diagnosis, or to achieve a desired therapeutic effects such as to modify, restore, or improve neural function. The modifying agents may include electrical, magnetic, or other forms of energy.

In an example, the IND 110 may include a hermetically sealed can, which houses circuitry for generating the electrostimulation pulses, control circuitry, communication circuitry, and a battery, among other components. The electrostimulation pulses may be characterized by specified intensity, frequency, waveform, among other parameters, and may be used for stimulating a region of a spinal cord tissue (which may include, by way of example and not limitation, dorsal column, dorsal horn, spinal nerve roots such as the dorsal nerve root, and dorsal root ganglia), a region of a brain, or a peripheral nerve tissue. The IND 110 may be configured to be operably coupled to one or more leads that may be surgically placed in a specified position for the IND 110 to generate and deliver neuromodulation energy to a targeted region (e.g., volume of activation) of neural tissue, such as a brain, a spinal cord, or a peripheral neutral target tissue.

FIG. 1 generally illustrates, by way of example and not limitation, a neuromodulation lead 124. The lead 124 may include respective one or more electrodes electrically coupled to the IND 110. In an example, the lead 124 may be a directional lead that includes at least some segmented electrodes circumferentially disposed about the directional lead. Two or more segmented electrodes may be distributed along a circumference of the lead. The actual number and shape of leads and electrodes may vary according to the intended application. Detailed description of construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are incorporated herein by reference.

The neuromodulation system 100 may include an external system 130 that may communicate with the IND 110 such as via a communication link 103. The external system 130 may be an external programming system which may be configured to program the IND 110 and receive information about one or more signals acquired by IND 110 via a communication link 103. The external programming system may include a dedicated hardware/software system such as a programmer or a remote server-based patient management, or alternatively be defined predominantly by software running on a standard personal computer (PC). As generally illustrated in FIG. 1, the external system 130 may include a user interface unit 131, a programmer circuit 134, and a lead orientation estimator 135.

The user interface unit 131 may include a display screen 132 and may include a user input circuit 133. The external system 130 may display information on the display screen including parameters associated with programming of the IND 110, operational status of the IND 110, and the lead(s) (e.g. the lead 124) such as lead impedance or lead integrity indicators, battery status of the IND 110 such as battery longevity indicators, among others. The external system 130 may be coupled to a system, other than the IND 110, that may acquire, and/or store information about the operation of the IND 110 or the lead(s) (e.g., the lead 124). For example, the external system 130 may be coupled to an imaging system, such as an X-ray machine, a computed tomography (CT) scanner, or a magnetic resonance imaging (MRI) system, to display an image of a portion of the lead under the X-ray, the CT scan, or the MRI scan. In another example, the external system 130 may be coupled to a machine-readable medium such as a memory device, such as an electronic medical record (EMR) system, that stores image data of a portion of the lead. The information displayed at the display screen 132 may be presented in a human-perceptible medium format, including a reconstructed digital image, a diagram, a table, a chart, or other textual, tabular, or graphical presentation of operational status of the IND 110 or the lead 124.

The user input circuit 133 may include an input device that enables the system user to control the elements displayed on the display screen 132. The input device may include a keyboard, on-screen keyboard, mouse, trackball, touchpad, touch-screen, or other pointing or navigating devices. In an example, the input device may enable the system user to select and edit a portion of the image of the lead, such as to zoom, pan, or rotate the image of the lead, or switch from one view or viewing angle to another view or viewing angle of the image of the lead. The input device may also enable the system user to manually perform at least a part of the lead template generation process, or to confirm, override, or otherwise modify the automatically generated lead template, examples of which are discussed below, such as with reference to FIGS. 5-7.

The user input circuit 133 may be coupled to a programmer circuit 134 to enable a system user to program the IND 110 with desired parameters of neuromodulation therapy, or parameters for sensing a physiologic signal from the patient 150. Examples of the neuromodulation parameters may include stimulation amplitude, frequency, pulse width, duty cycle, duration, electrode polarity and configuration, sequence of stimulation, waveforms, a number of pulses in a train of pulses, a duration of the train of pulses, a pulse train-to-pulse train interval, a pattern of pulses, etc. The programmer circuit 134 may be a dedicated hardware/software system, or may be defined predominantly by software running on a standard PC. In an example as illustrated in FIG. 1, the programmer circuit 134 may be coupled to the lead orientation estimator 135, and determine a neuromodulation parameter set including stimulation electrode and vector configuration using at least the estimated lead orientation such as produced by the lead orientation estimator 135.

The lead orientation estimator 135 may determine an orientation of a lead, such as the lead 124, using image data of at least a portion of the lead. The image data of the lead may be obtained from an imaging system, or from a machine-readable medium such as a memory device configured to store the image data of the lead of interest. The lead orientation estimator 135 may determine the lead orientation using a template matching process, which includes image registration of a template image of a portion of the lead to a target image of the same portion of the lead. The template image of the lead may be predetermined and stored in the machine-readable medium. Alternatively, the lead orientation estimator 135 may include a template formulation circuit for generating the template of the lead or a portion of the lead. Examples of the lead orientation estimator 135, and the lead template formation circuit are described below, such as with reference to FIGS. 4-7.

In an example, the lead orientation estimator 135 may be implemented using instructions executable by a machine to provide human-perceptible information about the estimated lead orientation. The instructions may be stored in a machine-readable storage medium. In an example, at least a part of the machine-readable storage medium may be incorporated into the programmer circuit 134. The programmer circuit 134 may configure the display screen 132 to display the estimated lead orientation on the display screen 132, and to prompt a clinician to program the IND 110 with modulation parameters determined at least according to the estimated lead orientation.

The communication link 103 between the external system and the IND may include a wireless link such as an inductive telemetry link or a radio-frequency telemetry link. The communication link 103 may include multiple communication links and intermediate devices between the external system and the IND, where the multiple communication links may include a wired link, a telecommunication link such as an internet connection, or a wireless link such as one or more of an inductive telemetry link, a radio-frequency telemetry link. The communication link 103 may provide for data transmission between the IND 110 and the external system 130. The transmitted data may include, for example, real-time physiological data acquired by the IND 110, physiological data acquired by and stored in the IND 110, therapy history data or data indicating IND operational status stored in the IND 110, stimulation parameters to the IND 110, one or more programming instructions to the IND 110 which may include configurations for sensing physiologic signal or delivering electrostimulation, device self-diagnostic test, among others. In some examples, the IND 110 may be coupled to the external system 130 further via an intermediate control device, such as a handheld external remote control device to remotely instruct the IND 110 to generate electrical stimulation pulses in accordance with selected stimulation parameters produced by the external system 130.

Portions of the IND 110 or the external system 130 may be implemented using hardware, software, firmware, or combinations thereof. Portions of the IND 110 or the external system 130 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals. While described with reference to the IND 110, the neuromodulation system 100 could include a subcutaneous medical device, wearable medical devices, or other external medical devices.

Figure 2:
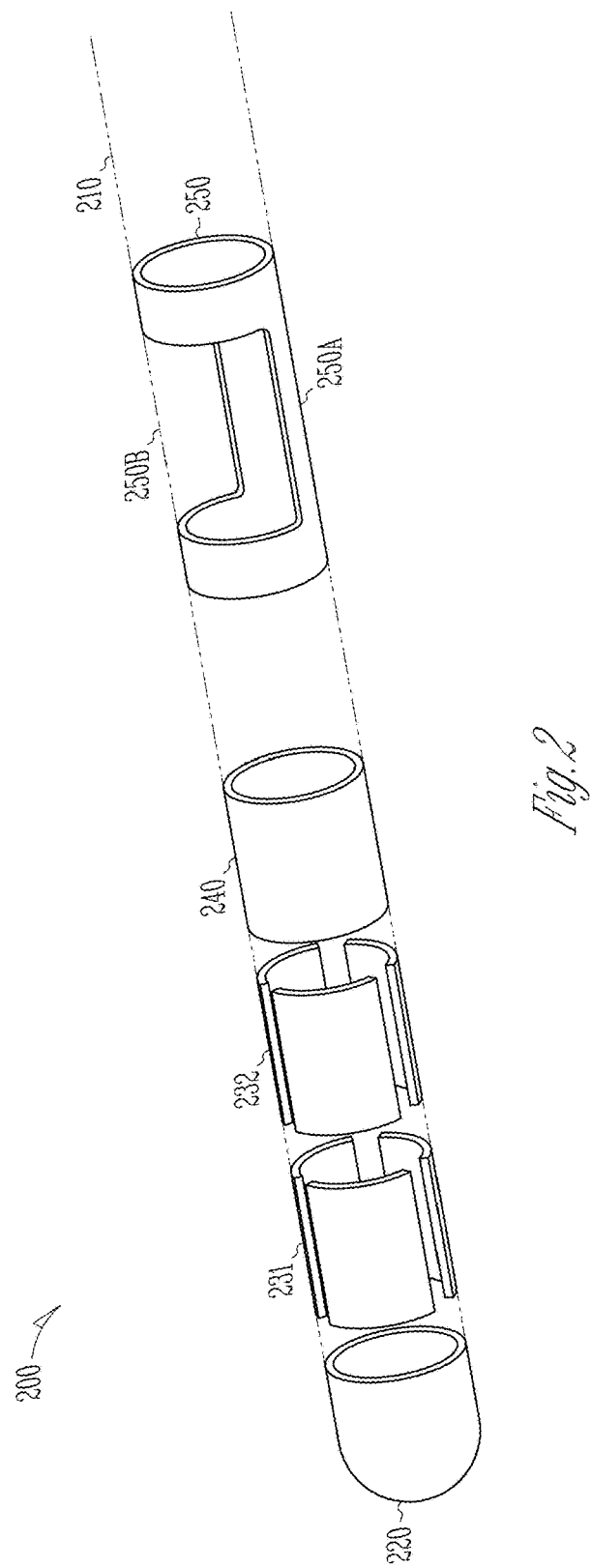
FIG. 2 illustrates, by way of example and not limitation, a directional lead with a marker.

FIG. 2 illustrates, by way of example and not limitation, a directional lead 200 with a marker. The illustrated directional lead 200 has an elongated cylindrical lead body 210 along a longitudinal lead axis, and includes insulative material coating that encloses wire conductors. The proximal end of the lead body 210 may include terminals that may be electrically coupled to the wire conductors and receive electrostimulation pulses from the IND 110. The directional lead 200 may include a plurality of electrodes disposed on the lead body 210 and electrically coupled to respective wire conductors, including a tip electrode 220 at the distal end of the lead and an axially disposed column electrode 240 (also known as a ring electrode) at the lead shaft. The directional lead 200 may include at least some segmented electrodes circumferentially disposed about the lead body 210, which may be used for directional stimulation of a target tissue. By way of non-limiting example, and as illustrated in FIG. 2, the directional lead 200 may include a first ring 231 of segmented electrodes 231a-231c distributed in a circumference of the lead body 210, and a second ring 232 of segmented electrodes 232a-232c distributed in another different circumference of the lead body 210. In an example, the segmented electrodes 231a-231c and 232a-232c may be disposed between the tip electrode 220 and the column electrode 240. In other examples, one or both rings of the segmented electrodes 231a-231c and 232a-232c may be more proximally disposed than the column electrode 240. The number, shape, and circumferential distribution of the segmented electrodes, as well as the relative longitudinal positions of the segmented electrodes with respect to the column electrode 240, may vary according to the intended application.

The directional lead 200 may include a marker 250 axially and circumferentially distributed on the lead body 210. The marker 250 may be configured to identify a rotational orientation about the longitudinal axis of the directional lead 200. In an example, the marker 250 is not electrically coupled to the IND 110, for either sensing a physiological signal or deliver modulation energy. The marker 250 may be more proximally disposed along the length of the lead than the plurality of electrodes 220, 231, 232, and 240 (as illustrated in FIG. 2), or at a different longitudinal position relative to the electrodes 220, 231, 232, and 240.

The marker may include a first portion that has a radiopaque band 250A around a circumference of the lead body 210 and a second portion that has a radiolucent window 250B. The relative circumferential positions between the marker band 250A and the marker window 250B may be indicative of the rotational orientation of the directional lead 200. In an example, the rotational orientation of the directional lead 200 may be represented by a directional vector perpendicular to the longitudinal axis of the directional lead 200 pointing outwards towards the marker in an image of the lead or an image of the marker. In some examples, the maker 250 can include a marker band 250A without the window such as the window 250B. The marker band 250A can be made of metal or other radiopaque compounds.

FIGS. 3A-B illustrates, by way of example and not limitation, a CT scan image 300 of a portion of the directional lead 200 from different viewing angles. The CT scan image 300 may be produced by a CT scanner when the directional lead 200 is positioned at the target site such as in the brain, the spinal cord, or other neural targets. The imaging axis of the scanner may be oriented at a particular angle with respect to the longitudinal axis of the directional lead 200. The CT scan image 300 may be displayed on the display screen 132, and controllably adjusted and edited by a system user through the user input circuit 133, including image zooming, highlighting, or changing a viewing angle, among other operations.

The CT scan image 300 may present images of the electrodes on the directional lead 200, including the tip electrode image 320 corresponding to the tip electrode 220, segmented electrodes image 331 corresponding to the ring 231 of the segmented electrodes 231a-c, segmented electrodes image 332 corresponding to the ring 232 of the segmented electrodes 232a-c, and the column electrode image 340 corresponding to the column electrode 240. The marker image 350 of the marker 250 may have a distinctive anisotropic shape. Under the CT scan, as illustrated in FIGS. 3A-B, the radiopaque band 250A has a convex shape of a bulge 350A protruding outwards radially away from the lead axis, and the radiolucent window 250B has a concave shape of a dimple 350B curving inward radially towards the lead axis. The different shapes of 350A and 350B correspond to the relative circumferential positions of the marker band 250A and the marker window 250B in the directional lead 200. As such, the CT scan image 300, or a portion of the image 300 such as the bulge 350A (corresponding to marker band 250A) or the dimple 350B (corresponding to the marker window 250B), may be used to identify a rotational orientation of the directional lead 200 about the longitudinal axis.

Figure 4:
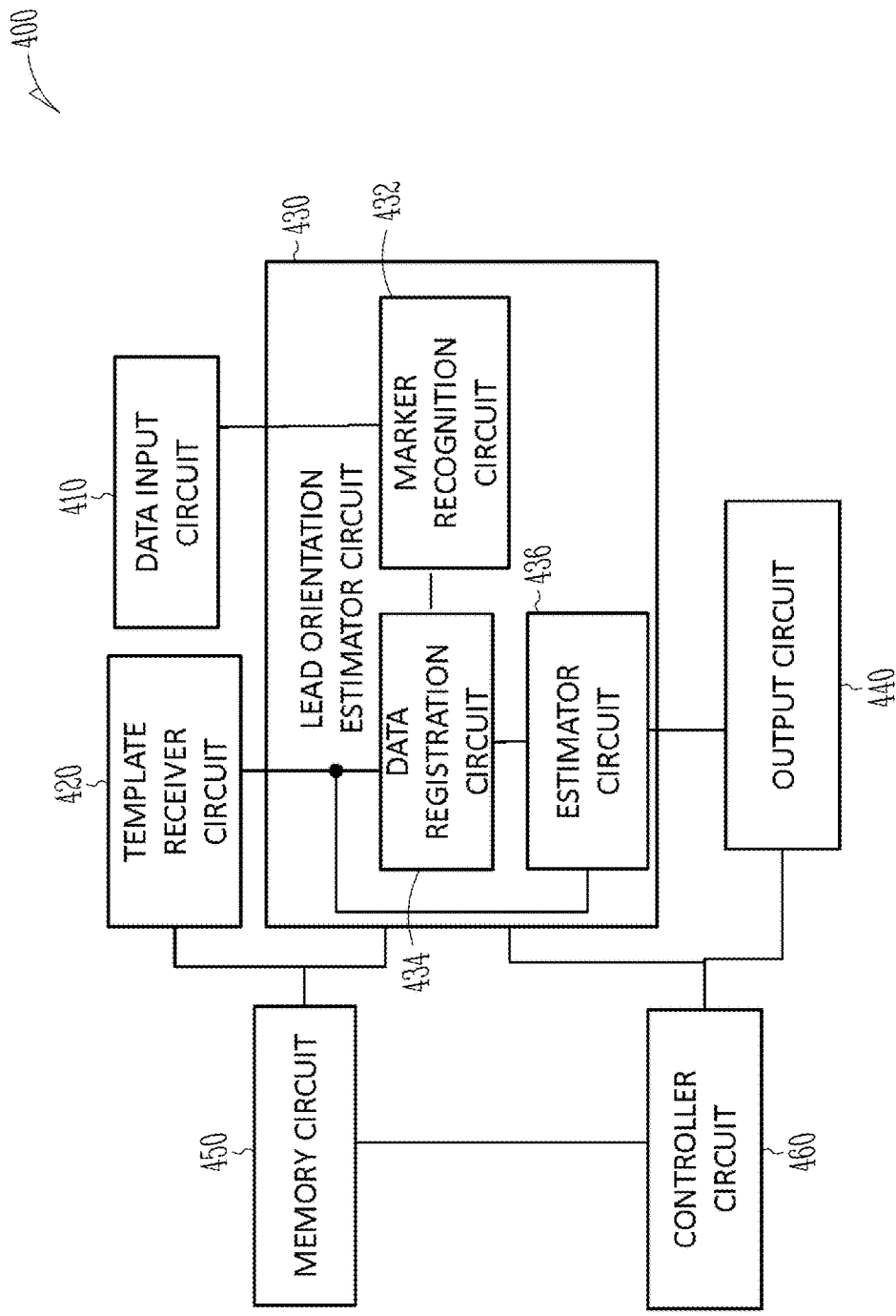
FIG. 4 illustrates, by way of example and not limitation, a lead orientation estimator circuit.

FIG. 4 illustrates, by way of example and not limitation, a lead orientation estimator 400, which may be an embodiment of the lead orientation estimator 135. The lead orientation estimator circuit 400 may include one or more of a data input circuit 410, a template receiver 420, a lead orientation estimator circuit 430, an output unit 440, a memory unit 450, and a controller circuit 460.

The data input circuit 410 may receive image data of at least a portion of a neuromodulation lead, such as the directional lead 200, that has a marker structure such as the marker 250 as shown in FIG. 2. The neuromodulation lead may have an unknown lead orientation. The data input circuit 410 may be coupled to an imaging system, or a machine-readable medium such as a memory circuit 450, to receive image data. In an example, the image data may include data of a computed tomography (CT) scan of the lead such as the CT scan image 300 of the lead 200, or the CT scan image 350 of the marker 250, as illustrated in FIGS. 3A-B. The image data may also include an X-ray image, an ultrasound image, a MIll image, a positron emission tomography (PET) image, or a single-photon emission computed tomography (SPECT) image, among others.

The template receiver circuit 420 may receive at least one template of a reference lead, such as a reference directional lead. The reference lead may be identical to, or of the same type of, the lead used for producing the image data received at the data input circuit 410. The template may be constructed using image data of the lead when the lead is substantially aligned with an imaging axis, and positioned with a specified and known rotational orientation. The image data used to construct the template may be obtained from the same type of imaging system used to produce the image data of the lead as received by the data input circuit 410. For example, if the image data received at the data input circuit 410 are from CT scan of the lead or a particular portion of the lead (such as the marker 250), then the template may be constructed using the CT scan of the lead or the same particular portion of the lead when the lead is positioned with a specified and known rotational orientation.

In an example, the template receiver circuit 420 may receive at least one template that has been created and stored in a machine-readable medium such as the memory circuit 450. In another example, the template receiver circuit 420 may be coupled to a template formation circuit configured to create at least one template using image data of a portion of the direction lead, such as the marker image 350 as shown in FIGS. 3A-B. The template formation circuit may be separated from the lead orientation estimator circuit 400, or included as a part of the lead orientation estimator circuit 400.

The template may include a reference data cube ($X_R$) of the marker and a reference marker direction vector ($v_R$) indicative of the specified rotational orientation of the lead about the longitudinal axis of the lead. The reference data cube ($X_R$) may be a selected portion of the image data extracted from the marker image 350 of a reference lead. In an example, the reference data cube ($X_R$) may be a three-dimensional (3D) data array of a volume of the marker image, such as the marker band image 350A. In some examples, the template may include other forms of data representation, in lieu of the data cube ($X_R$), that represent anisotropy of the maker image 350, such as an isosurface of the marker band image 350A. The reference marker direction vector ($v_R$) may be generated using the image data of the marker image 350 or the image data of the marker band image 350A. Examples of the template construction using the image data of the lead or a portion of the lead are discussed below, such as with reference to FIGS. 5 and 6.

The lead orientation estimator circuit 430 may be coupled to the data input circuit 410 and the template receiver circuit 420, and configured to estimate the lead orientation using the image data of a target lead such as received from the data input circuit 410 and the template provided by the template receiver circuit 420. The lead orientation estimator circuit 430 may include one or more of a marker recognition circuit 432, a data registration circuit 434, and an estimator circuit 436.

The marker recognition circuit 432 may identify the marker from the image data of the lead. In an example, the marker recognition circuit 432 may include an image segmentation module that may partition the image data of the lead into a plurality of segments that represent various structural elements on the lead, such as image segments corresponding to one of the electrodes 220, 231, 232, or 240, or the marker 250. In some embodiments, the data input circuit 410 may receive pre-segmented image data of the marker, instead of the image data of the entire lead. Segmentation module may therefore be excluded from the data registration circuit 434. As illustrated in FIGS. 3A-B, the marker 250 may have characteristic anisotropic shape 350 under the CT scan, which includes a bulge 350A protruding outwards, and a dimple 350B of curving inward, relative to the lead axis. The marker recognition circuit 432 may identify the marker by recognizing such anisotropic shape of the marker under the CT scan using the data of the image segments.

The marker recognition circuit 432 may further use the image data of the identified marker to produce a target data cube ($X_T$) of the marker. Similar to the reference data cube $X_R$ extracted from the marker image of the reference lead with a specified and known lead orientation, the target data cube $X_T$ may be extracted from a selected portion such as the marker image 350 of the target lead with a target, unknown lead orientation. In an example, $X_T$ may have a similar data structure as $X_R$, such as a 3D data array of a volume of the marker image such as the marker band image 350A corresponding to the target lead. Examples of the marker identification and construction of the target data cube $X_T$ are discussed below, such as with reference to FIG. 6.

The data registration circuit 434 may register the reference data cube $X_R$ to the target data cube $X_T$. Because both $X_R$ and $X_T$ have the same image data format and constructed into a similar data structure, the data registration circuit 434 may produce a transformation operator $\Phi$ for transforming $X_R$ into a transformed reference data cube $\Phi(X_R)$, or a "registered reference data cube." The transformation operator $\Phi$ may be an affine transformation. The affine transformation may include rigid transformations that preserve the distance, such as one or any combination of a translation, a rotation, or a reflection operation; or non-rigid transformations such as one or any combination of stretching, shrinking, or model-based transformations such as radial basis functions, splines, or finite element model. In some embodiments, the transformation may include both the rigid transformation to bring reference data cube $X_R$ in global alignment with the size and orientation of the target data cube $X_T$, and the non-rigid transformation to reduce the local geometric discrepancies by aligning the reference data cube $X_R$ with the target data cube $X_T$.

By registration, the transformed reference data cube $\Phi(X_R)$ may be in a coordinate system similar to that of the target data cube $X_T$. The data registration circuit 434 may determine the transformation operator $\Phi$ as one that causes the transformed reference data cube $\Phi(X_R)$ to match the target data cube $X_T$ within a specified margin. In an example, the transformation operator Φ may minimize the multidimensional distance between $\Phi(X_R)$ and $X_T$, such as when the distance falls below a specified threshold. Examples of the distance measure may include L1 norm, L2 norm (i.e., Euclidian distance), infinite norm, other norm in the normed vector space, or a dissimilarity measure between $\Phi(X_R)$ and $X_T$ such as correlation coefficient, mutual information, or ratio image uniformity.

The estimator circuit 436 may estimate the orientation, including a rotational orientation, of the lead using the reference marker direction vector $v_R$ of the template received by the template receiver circuit 420, and the transformation operator Φ as produced by the marker recognition circuit 432. In an example, the estimator circuit 436 may apply the transformation operator Φ to the reference direction vector $v_R$ to produce an estimated marker direction vector $\tilde{v}_T = \Phi(v_R)$. The estimated marker direction vector $\tilde{v}_T$ may be indicative of the rotational orientation of the lead relative to an imaging axis used for producing the image data of the at least a portion of the lead.

The output circuit 440 may produce a graphical representation of the lead and at least the estimated target marker direction vector $\tilde{v}_T$. The output circuit 400 may additionally produce graphical representations of the target marker, the reference marker of the template, the reference marker band direction vector, among others. The output circuit 440 may be coupled to the display screen 132 as shown in FIG. 1 to display the graphical representations of the lead, the estimated target marker direction vector $\tilde{v}_T$, or other information.

The controller circuit 460 may control the target lead image data operations at the data input circuit 410, the creation, storage, and retrieval of templates at the template receiver circuit 420, the lead orientation estimation at the least orientation estimator circuit 430, presentation generation at the output circuit 440, and the data flow and instructions among these components and respective subcomponents. In an example, the controller circuit 460 may control the communication between the lead orientation estimator 400 and the programmer circuit 134, the user interface unit 131, or an electrostimulator circuit in the IND 110 for generate directional electrostimulation for modulating the body tissue using the lead oriented at least according to the determined rotational.

Figure 5:
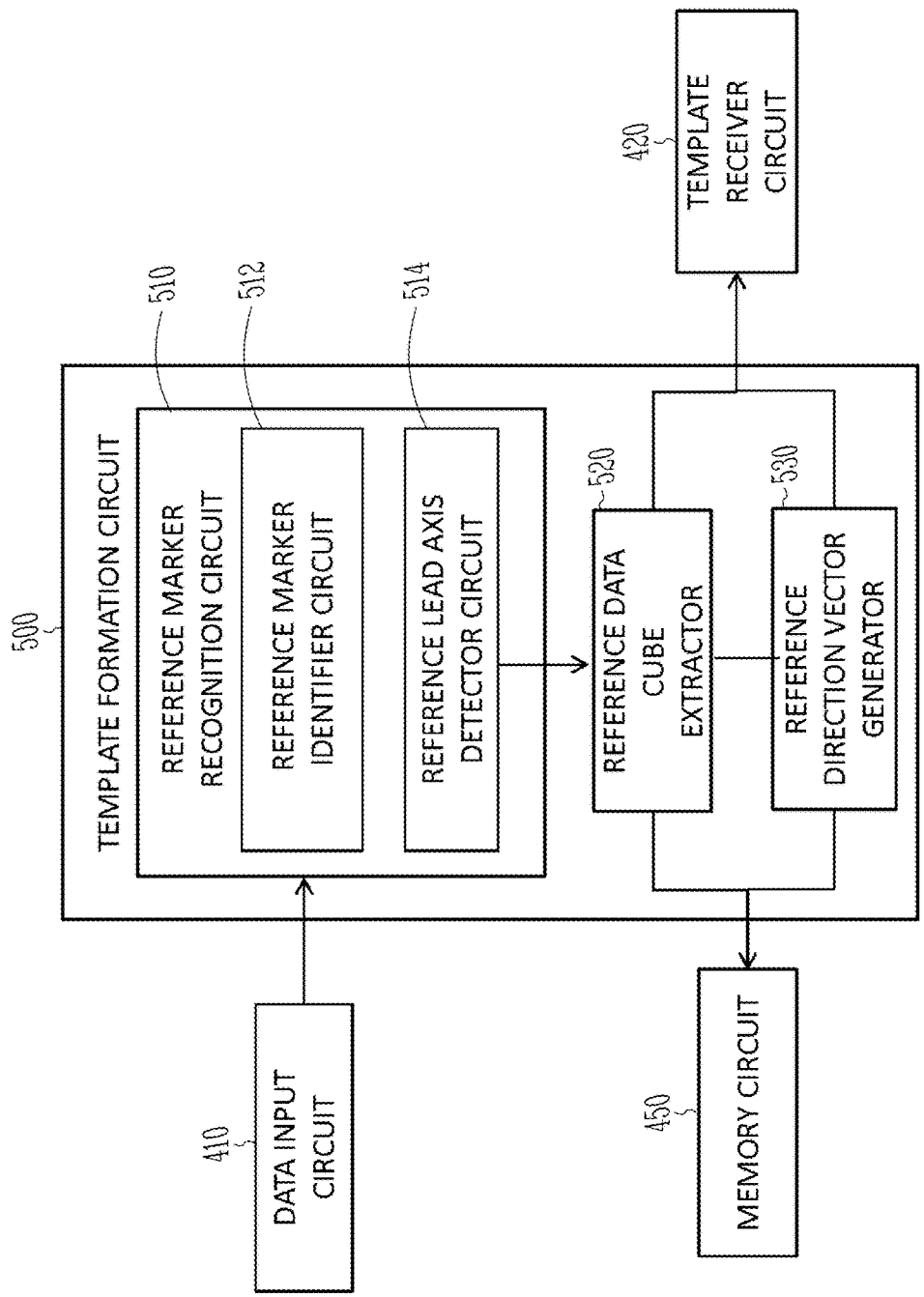
FIG. 5 illustrates, by way of example and not limitation, a template formation circuit and portions of an environment in which it operates.

FIG. 5 illustrates, by way of example and not limitation, a template formation circuit 500 and portions of the environment in which it operates. The template formation circuit 500 may be a standalone circuit separated from the lead orientation estimator circuit 400, or it may be integrated as a part of lead orientation estimator circuit 400. The template formation circuit 500 may include a reference marker recognition circuit 510, a reference data cube ($X_R$) extractor 520, and a reference direction vector generator 530. The reference lead has a marker such as the marker 250 has shown in FIG. 2. The image data may be from the same type of imaging system used to produce the image data of the lead as received by the data input circuit 410, such as image data of the CT scan of the lead when the lead is positioned with a specified and known rotational orientation.

The template formation circuit 500 may be coupled to the data input circuit 410 to receive image data of a reference lead obtained when the lead is substantially aligned with an imaging axis. The reference marker recognition circuit 510 may have a similar structure as the marker recognition circuit 432, and include a reference marker identifier circuit 512 and a reference lead axis detector circuit 514.

The reference marker recognition circuit 510 may optionally include an image segmentation circuit to partition the image data of the reference lead into a plurality of segments representing various structural elements including the electrodes (such as one or more of the electrodes 220, 231, 232, and 240 shown in FIG. 2) and the marker (such as marker 250 shown in FIG. 2). The image segmentation circuit may be excluded from the reference data registration circuit 434 if the input circuit 410 receives data of segmented image of the marker, instead of the image data of the entire lead. Similar to the marker recognition circuit 432, the reference marker identifier circuit 512 may identify the marker by recognizing the anisotropic shape of the marker, such as marker band image 350A and maker window image 350 of a CT scan, as illustrated in FIGS. 3A-B.

The reference lead axis detector circuit 514 may automatically identify a lead tip and a lead shaft from the image segments of the lead, and detect a reference lead axis 620 such as by joining the identified lead tip and lead shaft. In an example, the reference marker recognition circuit 510 may be coupled to the user interface unit 131, and an image of the lead used for forming a template may be displayed on the display screen 132. A system user may identify the lead tip and the lead shaft from the displayed image of the lead, and provide input to the reference lead axis detector circuit 514 about the positions such as coordinates of the lead tip and the lead shaft, and the reference marker recognition circuit 510 may detect the reference lead axis 620 by joining the user-provided lead tip and lead shaft.

Figure 6B:
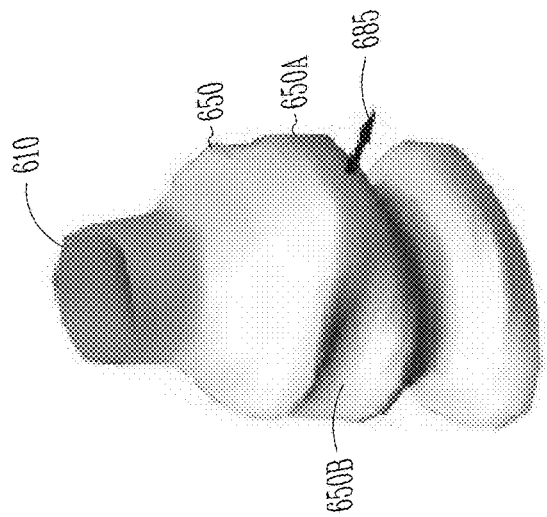
Figure 6A:
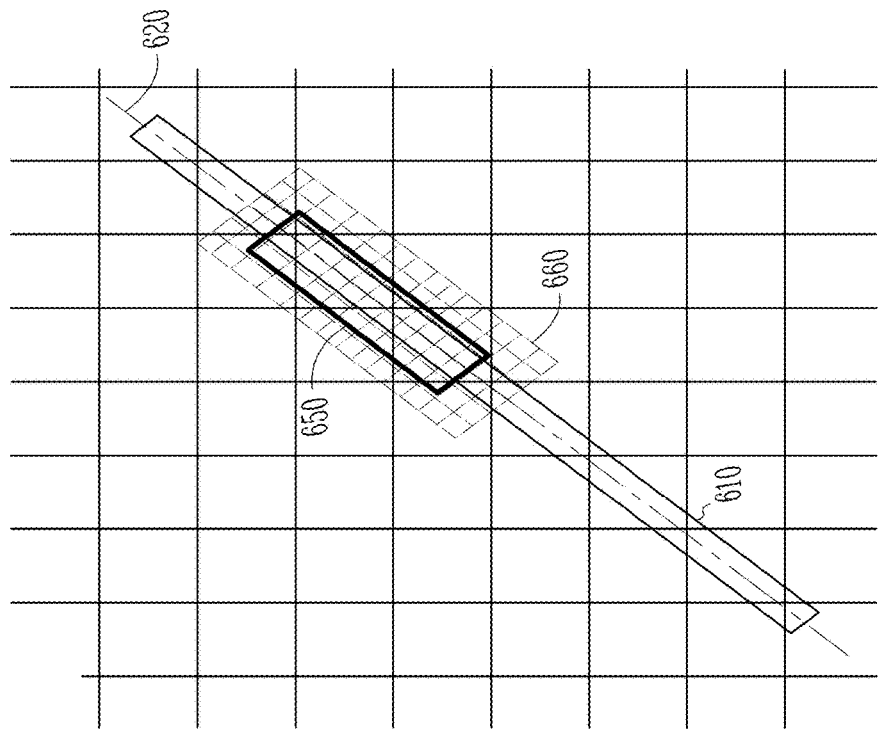

The reference data cube extractor 520 may produce the reference data cube $X_R$ of the template using the image data of the marker as identified by the reference marker identifier circuit 512 and the detected lead axis as provided by the reference lead axis detector circuit 514. By way of non-limiting example, FIG. 6A illustrates a schematic of a data cube formed out of the marker 650 along the lead shaft 610. The reference data cube 660 may include image data within a volume of a specified shape, dimension, and orientation with respect to the identified lead axis 620, such as a cylindrical volume containing the marker 650 and axially aligned with the detected lead axis 620. In other examples, the reference data cube 660 may be sized and shaped to cover a portion of the lead image such as the bulge corresponding to the marker band, or to cover the entire lead. Depending on the property of the image of the lead as received from the data input circuit, the reference data cube 660 may in some examples include a 2D data array representing a 2D image of at least a portion of the reference lead.

The reference data cube extractor 520 may include a resampling module that resamples the image data of the reference data cube 660. In an example, the image data of the reference data cube may be up-sampled to have a higher spatial resolution (as illustrated by finer or smaller grid within the reference data cube 660 in FIG. 6A) than the original spatial resolution of the image of the lead (as illustrated by coarser or larger grid outside the reference data cube 660 in FIG. 6A). Examples of the up-sampling to improve the spatial resolution may include pixel interpolation, spatial filtering, among other methods. In an example, the reference data cube 660 may have an isotropic spatial resolution of approximately 0.1 mm. The lead axis detection and the data cube formation as discussed above may also be used by the marker recognition circuit 432 to produce the target data cube $X_T$.

The reference direction vector generator 530 may use the reference data cube $X_R$ to determine the reference direction vector $v_R$, which may be indicative of the rotational orientation of the lead with respect to the lead axis. Referring to FIG. 6B, which illustrates a portion of the CT scan image of the lead, including images of the lead shaft 610, the bulge 650A corresponding to the marker band 250A, and the dimple 650B corresponding to the maker window 250B. The reference direction vector 685, determined using the reference data cube $X_R$ 660, is shown as an arrow pointing outwards radially from the bulge of the marker.

The reference direction vector generator 530 may determine the reference direction vector $v_R$ using the extracted reference data cube $X_R$. FIGS. 6C-D illustrate two methods used by the reference direction vector generator 530 to determine the $v_R$. In FIG. 6C, a midpoint 630 of the reference marker 650 may be detected using the identified lead tip and the lead shaft, and the known dimensional information such as the longitudinal position of the marker relative to the lead tip. A bulging point 670 within the identified marker 650 may be automatically, or based on a user input, determined as a point on the bulge 650A of the marker that is spatially farther away from the midpoint 630 of the marker than some other points within the identified marker 650. An initial marker direction vector 675, which originates at the midpoint 630 of the marker and points to the bulging point 670, may then be generated. A projection plane 692 may be determined that is perpendicular to the detected lead axis 620 and across the midpoint 630. The reference direction vector generator 530 may project the initial marker direction vector 675 onto the projection plane 692, resulting in a projected vector 685 that points to a bulging point 680 within the maker 650. Such a projected vector 685 may be determined as the reference direction vector $v_R$.

Another method that the reference direction vector generator 530 may use to determine the reference direction vector $v_R$ may be visualized using the illustration in FIG. 6D A symmetric plane 694 through the detected lead axis 620 may be identified, such that the image data of the marker is substantially reflective symmetric about the symmetric plane 694. Two candidate marker direction vectors, 681 and 682, may be produced along the symmetric plane 694. Both candidate marker direction vectors 681 and 682 originate from and perpendicular to the lead axis 620, but point to two opposite directions. The reference direction vector generator 530 may make a comparison of the two candidate marker direction vectors 681 and 682 to identify one candidate direction vector (e.g., candidate vector 681 in FIG. 6D) that is spatially closer to the bulge 650A (such as the automatically detected or user-specified bulging point 670) than the other of the two candidate marker direction vector (e.g., candidate vector 682). The reference direction vector generator 530 may then determine the candidate vector spatially closer to the bulge 650A (e.g., candidate vector 681), as the reference direction vector $v_R$.

In some examples, the reference direction vector generator 530 may perform eigenvalue decomposition of an initial marker direction vector generated automatically or based on a user input, such as the initial marker direction vector 675, and determine the reference direction vector $v_R$ using an eigenvector produced by the eigenvalue decompensation. The reference direction vector generator 530 may additionally or alternatively produce a morphologic characterization of a portion of the marker, such as a curvature of the bulge 650A, and determine the reference direction vector $v_R$ using at least the curvature of the bulge 650A.

The reference data cube $X_R$ as produced by the reference data cube extractor 520 and the reference direction vector $v_R$ as produced by the reference direction vector generator 530, may be stored in the memory circuit 450. The $X_R$ and $v_R$ may also be received by the template receiver circuit 420, and used by the lead orientation estimator 400 to estimate the orientation of the lead.

Figure 7:
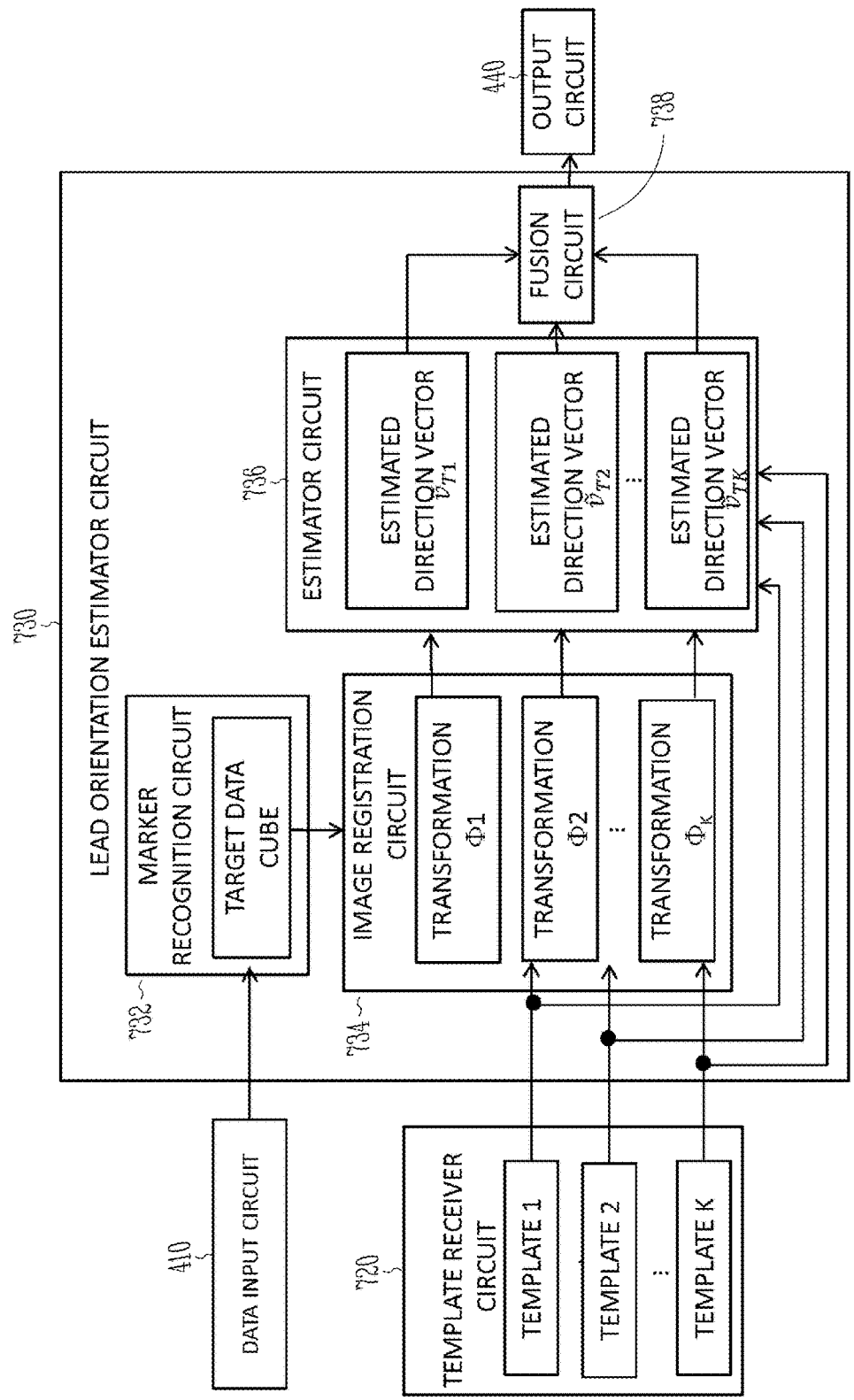
FIG. 7 illustrates, by way of example and not limitation, a lead orientation estimator circuit based on multi-atlas registration.

FIG. 7 illustrates, by way of example and not limitation, a lead orientation estimator circuit 730 based on multi-atlas registration. The lead orientation estimator circuit 730 may be an embodiment of the lead orientation estimator circuit 430. The lead orientation estimator circuit 730 may be coupled to the data input circuit 410 to receive image data of at least a portion of a lead, such as the directional lead 200, with a target, unknown lead orientation. The lead orientation estimator circuit 730 may include a marker recognition circuit 732, which may be an embodiment of the marker recognition circuit 432, which is configured to produce a target data cube $X_T$. The lead orientation estimator circuit 730 may include an image registration circuit 734 coupled to a template receiver circuit 720 to receive two or more templates (e.g., Template 1, Template 2, ..., Template K) of the lead. Each template includes a respective reference data cube $X_R$ and the corresponding reference direction vector $v_R$. In an example, at least one template may be formed by the template formation circuit 500 as previously discussed with reference to FIGS. 5 and 6. In some examples, one or more of the templates may include other forms of data representation, in lieu of the data cube ($X_R$), that represent anisotropy of the maker image, such as an isosurface of the marker band image.

The image registration circuit 734 may perform a multi-atlas registration, including registering at least some of the reference data cubes $\{X_{R1}, X_{R2}, \ldots, X_{RK}\}$ associated with the respective two or more templates {Template 1, Template 2, ..., Template K} to the target data cube $X_T$, such as by using image segmentation and image transformation as previously discussed with reference to the data registration circuit 434 in FIG. 4. The image registration circuit 734 may perform image registration, and produce two or more transformation operators $\{\Phi_1, \Phi_2, \ldots, \Phi_K\}$ corresponding to the respective templates {Template 1, Template 2, ..., Template K}. Each transformation operator $\Phi_i$ transforms the corresponding reference data cube $X_{Ri}$ into a transformed reference data cube $\Phi_i(X_{Ri})$ that matches $X_T$ within a specified margin, such as a multi-dimensional distance or a dissimilarity measure between $\Phi_i(X_{Ri})$ and $X_T$ falling below a specified threshold.

The lead orientation estimator circuit 730 may include an estimator circuit 736 that may generate two or more estimated marker direction vector $\{\tilde{v}_{T1}, \tilde{v}_{T2}, \ldots, \tilde{v}_{TK}\}$ of the lead by applying transformation operators $\{\Phi_1, \Phi_2, \ldots, \Phi_K\}$ to the respective reference direction vectors $\{v_{R1}, v_{R2}, \ldots, v_{RK}\}$, that is, $\tilde{v}_{Ti} = \Phi_i(v_{Ri})$. A fusion circuit 738 may determine a combined estimate $\tilde{v}_T$ of the marker direction vector rotational orientation of the direction lead using a fusion function $f$ of at least some of the two or more estimated direction vectors $\{\tilde{v}_{T1}, \tilde{v}_{T2}, \ldots, \tilde{v}_{TK}\}$, that is, $\tilde{v}_T = f(\tilde{v}_{T1}, \tilde{v}_{T2}, \ldots, \tilde{v}_{TK})$. The fusion function may be a linear or a nonlinear operator, including an averaging, a weighted average, a decision tree, a voting model, a regression model, a neural network model, a fuzzy logic model, a neural network model, or a support vector machine model, among others. Compared to an individual $\tilde{v}_{Ti}$, the combined estimate of the marker direction vector $\tilde{v}_T$ may more be a more accurate and reliable indicator of the rotational orientation of the lead. In an example, the fusion circuit 738 may additionally produce a confidence indicator such as a confidence bound of the estimated rotational orientation of the lead using the two or more estimated marker direction vectors.

The combined estimate of the marker direction vector $\tilde{v}_T$, and the confidence bound of $\tilde{v}_T$, may be passed to the output circuit 440 to produce graphical representations of $\tilde{v}_T$ and optionally along with other information including the target marker, the reference marker of the template, the reference marker band direction vector, etc.

Figure 8:
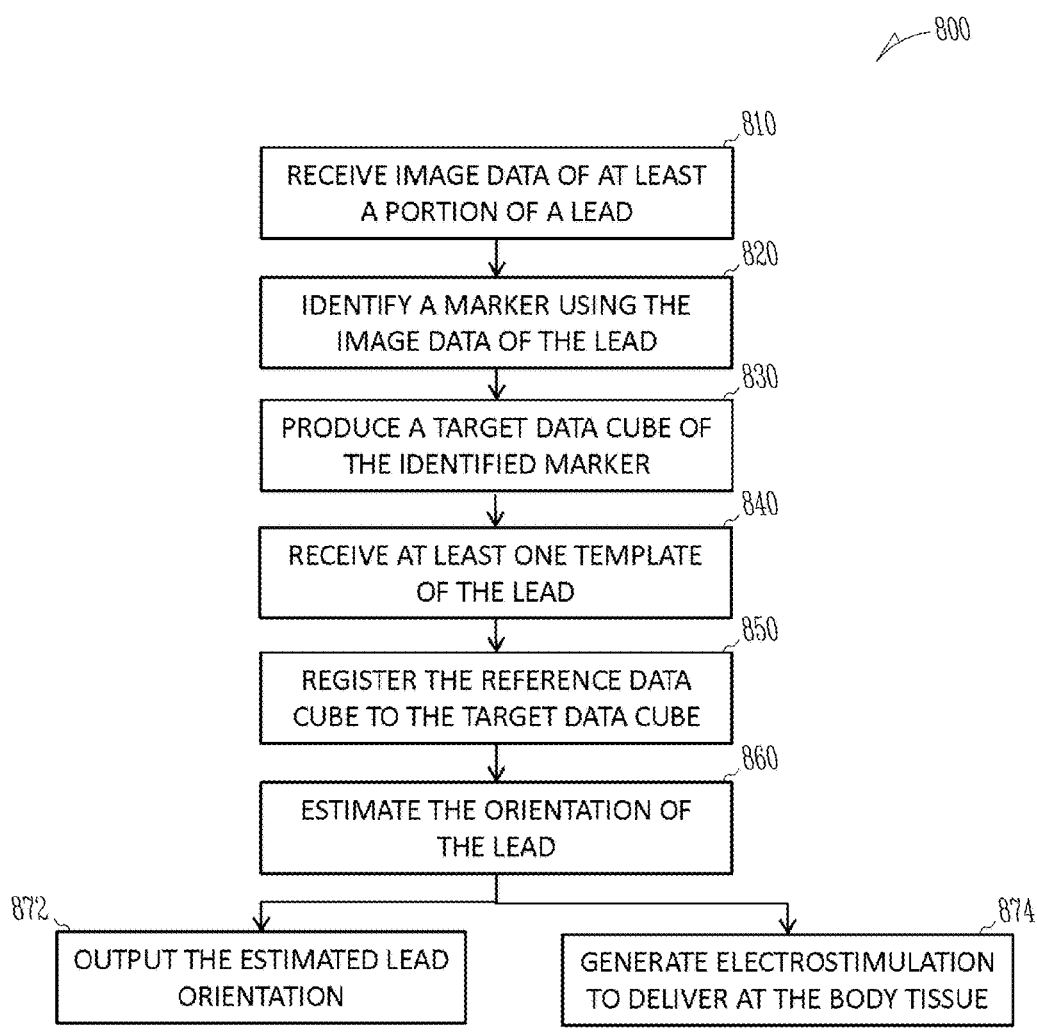
FIG. 8 illustrates, by way of example and not limitation, a method that includes estimating an orientation of a lead.

FIG. 8 illustrates, by way of example and not limitation, a method 800 that includes estimating an orientation of a lead. The method 800 may be implemented and operate in a medical system, such as a programming system or a remote server-based patient management system in communication with an ambulatory medical device (AMD) configured to provide electrical therapy to the patient. In an example, the method 800 may be implemented in and executed by the external system 130 to determine the orientation of the implantable lead 124 for SCS, and to provide a recommendation of modulation therapy using the orientation of the lead. The method may be used intraoperatively to determine location and orientation of lead placement to achieve desired electrode-tissue contacts, or during patient follow-ups to adjust of modulation therapy based at least on the information about lead orientation.

The method 800 begins at step 810, where image data of at least a portion of a lead is received, such as from an imaging system such as an X-ray machine, a CT scanner, a MRI scanner, a positron emission tomography (PET) scanner, a single-photon emission computed tomography (SPECT) scanner, among others. Alternatively, the image data may be received from a machine-readable medium such as a memory circuit 450. The lead may have a marker structure including a radiopaque marker band, such as the directional lead shown in FIG. 2. The lead is positioned in target tissue structures with a target, unknown lead orientation. In an example, the image data may include CT scan image of at least a portion of the lead including image data of the marker structure, such as illustrated in FIGS. 3A-3B.

At 820, the marker may be identified using the image data of the lead, such as by using the marker recognition circuit 432 as shown in FIG. 4. The input image of the lead may be segmented, and a characteristic anisotropic shape of the marker portion on the lead may be identified. As the example shown in FIG. 3, the marker under the CT scan has a bulge 350A protruding outwards, and a dimple 350B of curving inward, relative to the lead axis.

At 830, a target data cube $X_T$, corresponding to the identified marker on the lead, may be produced. Lead tip and lead shaft of the lead may be automatically, or at least based on a user's input, identified using the image segments of the lead. A lead axis may be detected such as by joining the identified lead tip and lead shaft. The target data cube $X_T$ may then be produced using image data of the marker and the detected lead axis. As illustrated in FIG. 6, the target data cube $X_T$ may be sized, shaped, and oriented to contain the marker image and be axially aligned with the detected lead axis. Alternatively, the target data cube $X_T$ may be sized, shaped, and oriented to cover only the bulge of the marker corresponding to the marker band, or the entire lead. Depending on the property of the image of the lead, in some example, the target data cube $X_T$ may be a 2D data array. In an example, the image data within the target data cube may be resampled to have a higher spatial resolution than that of the image of the lead.

At 840, at least one template of the lead may be received, such as from a machine-readable medium such as the memory circuit 450, or a template formation circuit. The reference lead may be identical to, or of the same type of, the lead used for producing the image data received at the data input circuit 410. The template may be constructed using image data of the lead when the lead is substantially aligned with an imaging axis and positioned with a specified and known rotational orientation. The template may include a reference data cube ($X_R$) of the marker and a reference marker direction vector ($v_R$) indicative of the specified rotational orientation of the lead about the longitudinal axis of the lead. The reference data cube $X_R$, similar to the target data cube $X_T$, may be a selected portion of the image data extracted from the marker image, and has similar data structure as the target data cube $X_T$, such as a 3D data array. In some examples, in lieu of the reference data cube $X_R$ and the target data cube $X_T$, other forms of data representation that represent anisotropy of the maker image can be used. For example, an isosurface of the identified marker band can be produced at 830, and an isosurface of the marker of the template can be received at 840.

At 850, the reference data cube $X_R$ may be registered to the target data cube $X_T$, to produce a transformation operator ($\Phi$) for transforming $X_R$ into a transformed reference data cube $\Phi(X_R)$, or a "registered reference data cube." The transformation may include an affine transformation such as a rigid transformation (such as one or any combination of translation, a rotation, or a reflection operation), non-rigid transformation (such as one or any combination of stretching, shrinking, or model-based transformations), or a combination of rigid and non-rigid transformations. The transformation operator $\Phi$ may be determined when the registered reference data cube $\Phi(X_R)$ matches the target data cube $X_T$ within a specified margin, such as when multi-dimensional distance or a dissimilarity measure between $\Phi(X_R)$ and $X_T$ falling below a specified threshold.

At 860, the orientation of the direction lead may be estimated using the reference marker direction vector $v_R$ and the transformation operator $\Phi$. In an example, the transformation operator $\Phi$ may be applied to the reference direction vector $v_R$ to produce an estimated marker direction vector $\tilde{v}_T = \Phi(v_R)$, which is indicative of the rotational orientation of the lead relative to an imaging axis used for producing the image data of the at least a portion of the lead.

At 872, a graphical representation of the estimated orientation of the lead, represented by $\tilde{v}_T$, may be produced, and displayed such as on the display screen 132 of the user interface unit. Other information, including the target marker, the reference marker of the template, or the reference marker band direction vector, may also be displayed. Additionally or alternatively, at 874, the determined orientation of the lead may be used to produce a recommendation of lead positioning, and providing directional electrostimulation to the body tissue using the two or more directional electrodes on the lead oriented at least according to the determined rotational orientation.

In some examples, the method 800 may be modified to perform orientation estimation based on multi-atlas image registration. For example, at 840 two or more templates of the lead, {Template 1, Template 2, . . . , Template K}, may be received, each template including a respective reference data cube $X_R$ and the corresponding reference direction vector $v_R$. At 850, the reference data cubes {$X_{R1}$, $X_{R2}$, . . . , $X_{RK}$} associated with the respective two or more templates may be registered to the target data cube $X_T$, and the corresponding transformation operators {$\Phi_1$, $\Phi_2$, . . . , $\Phi_K$} can be produced. At 860, two or more estimated marker direction vector {$\tilde{v}_{T1}$, $\tilde{v}_{T2}$, . . . , $\tilde{v}_{TK}$} of the lead may be estimated, such that $\tilde{v}_{Ti} = \Phi_i(v_{Ri})$ for at least some of the templates. A combined estimate $\tilde{v}_T$ of the marker direction vector rotational orientation of the direction lead using a fusion function $f$ of at least some of the two or more estimated direction vectors $\{\tilde{v}_{T1}, \tilde{v}_{T2}, \ldots, \tilde{v}_{TK}\}$. A confidence bound of the estimated rotational orientation of the lead may also be estimated using the two or more estimated marker direction vectors.

Figure 9:
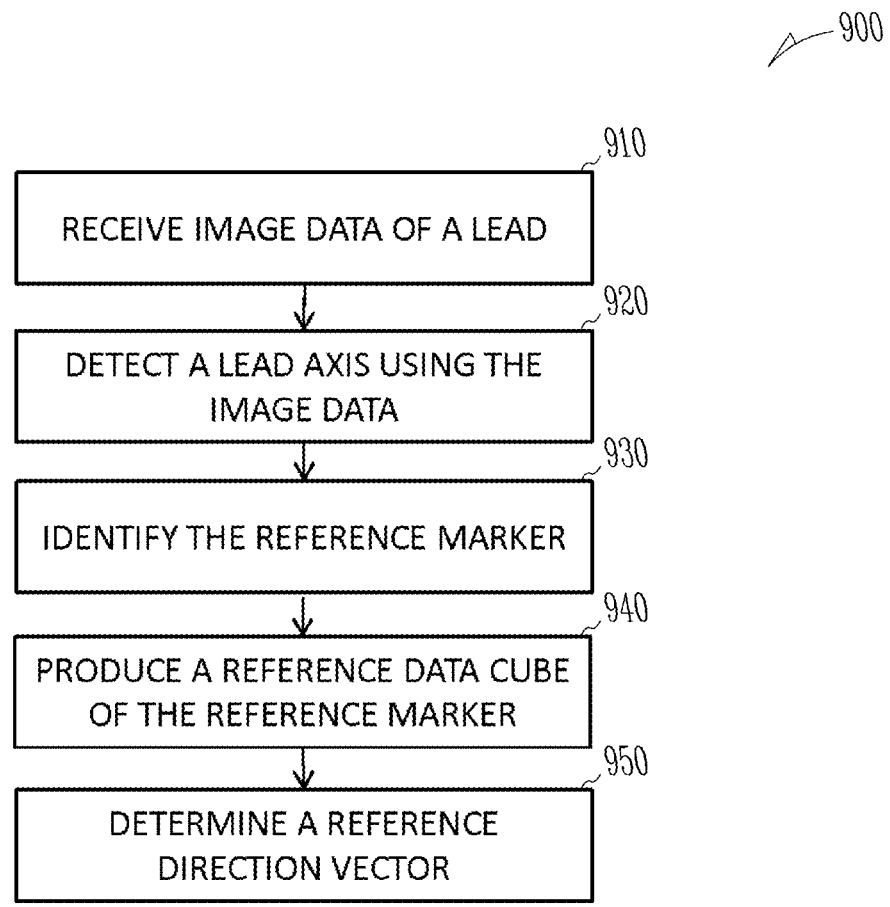
FIG. 9 illustrates, by way of example and not limitation, a method for automatic lead template generation for a lead.

FIG. 9 illustrates, by way of example and not limitation, a method 900 for automatic lead template generation for a lead. The method 900 may be implemented in and executed by the template formation circuit 500.

The method 900 begins at 910, where image data of the lead may be received. The image data of the lead may be obtained by using an imaging system when the lead is substantially aligned with an imaging axis. The image data may be from the same type of imaging system used to produce the image data of the lead, such as image data of the CT scan of the lead when the lead is positioned with a specified and known rotational orientation.

At 920, a lead axis may be detected using the image data of the lead. The image of the lead may be segmented, and a lead tip and a lead shaft may be automatically identified from the image segments of the lead. In an example, the image of the lead may be displayed on the display screen, and a system user may identify the lead tip and the lead shaft from the image of the lead and provide input about the positions such as coordinates of the lead tip and the lead shaft. A reference lead axis may be formed such as by joining the identified lead tip and lead shaft.

Figure 3:
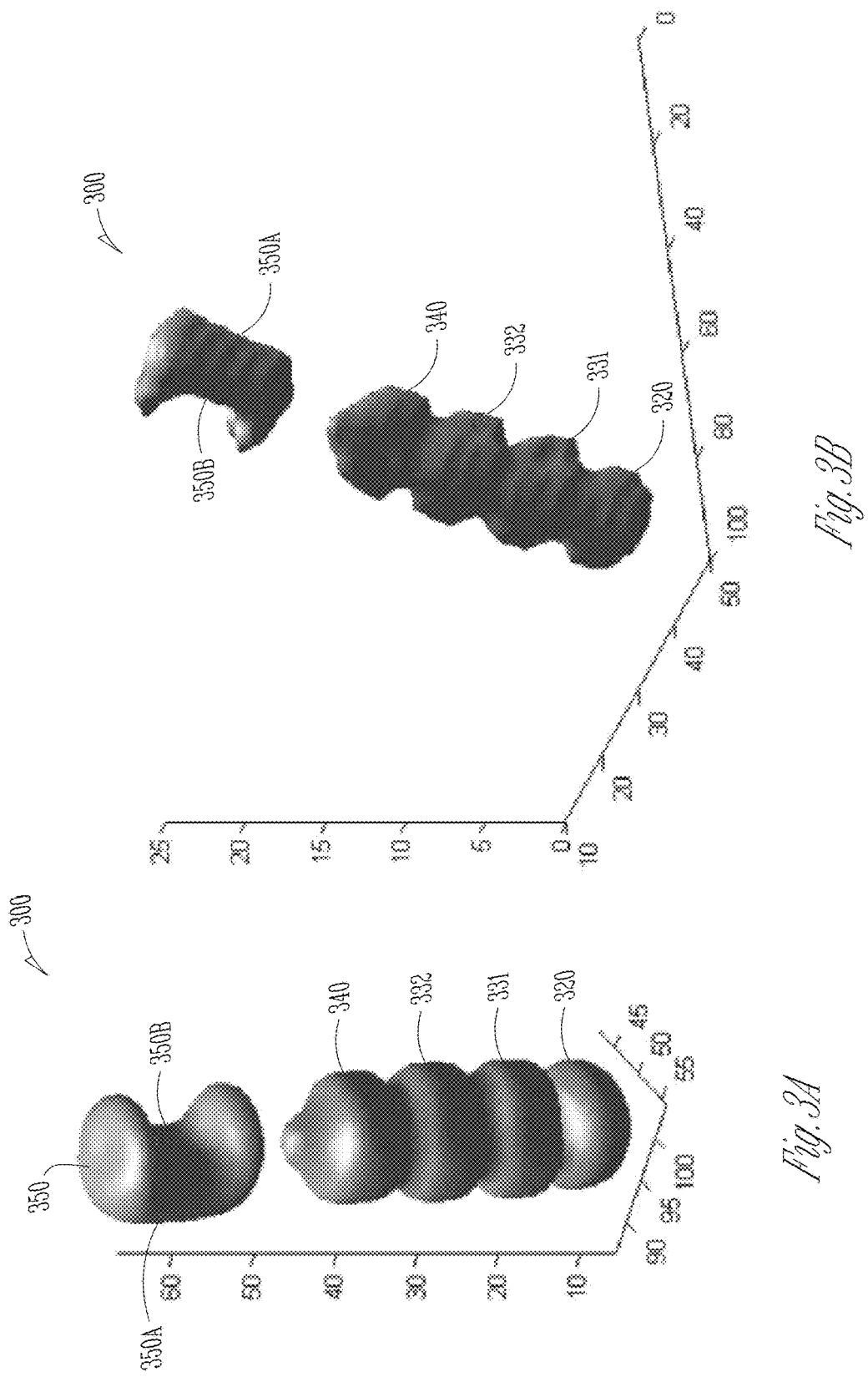
FIGS. 3A-B illustrate, by way of example and not limitation, images from a computerized tomography (CT) scan of a portion of a directional lead from different viewing angles.

At 930, the reference marker structure may be identified from the image data, at least based on anisotropic shape of the marker (such as the characteristic anisotropic shape 350 under the CT scan as shown in FIG. 3) using the data of the image segments.

At 940, a reference data cube $X_R$ of the reference marker may be produced using the image data of the marker and the detected lead. With reference to FIG. 6A, the reference data cube $X_R$ may have a specified dimension and orientation with respect to the identified lead axis. The dimension of the reference data cube $X_R$ may contain the marker and is aligned with the detected lead axis, or only covers a portion such as the bulge of the marker corresponding to the marker band, or the entire lead. The step 940 may also include resampling the image data within the target data cube to have a higher spatial resolution than that of the image of the lead.

At 950, a reference direction vector $(v_R)$ may be determined using the reference data cube $X_R$. The reference direction vector $(v_R)$ may be indicative of the rotational orientation of the lead with respect to the lead axis. In one example with reference to FIG. 6C, the method 950 includes detecting a midpoint of the marker using the identified lead tip and the lead shaft. A bulging point within the identified marker may be detected as a point spatially farther away from the midpoint of the marker than other points within the identified marker. An initial marker direction vector may be generated, which originates at the midpoint of the marker and points to the bulging point. A reference direction vector $(v_R)$ may then be determined as a projection of the initial marker direction vector onto a plane perpendicular to the detected lead axis.

In another example with reference to FIG. 6D, a symmetric plane through the detected lead axis may be identified. The image data of the marker may be substantially reflective symmetric about the symmetric plane. Two candidate marker direction vectors may be formed along the symmetric plane. Each of two candidate marker direction vectors is perpendicular to the lead axis, originates from and points to two opposite directions. The reference direction vector $(v_R)$ may be determined as one of the two candidate marker direction vectors that is spatially closer to a bulging point within the identified marker than the other of the two candidate marker direction vectors.

In some examples, the method 950 includes eigenvalue decomposition of an initial marker direction vector generated automatically or based on a user input, and determining the reference direction vector $v_R$ using an eigenvector produced by the eigenvalue decomposition. Morphologic characterization of a portion of the marker, such as a curvature of the bulge 650A, may be used to determine the reference direction vector $v_R$ using at least the curvature of the bulge 650A.

In some examples, the method 800, or variants of any part of the method 800 such as the method 900, may be implemented as instructions stored in a machine-readable storage medium. The machine may be in a form of a computer system, which may include a processor, memory, video display unit, an alpha-numeric input device, a user interface with a navigation device, a disk drive unit, a signal generation device, a network interface device, among others. The instructions may cause machine to perform any part of the methods 800 or 900 or any variants thereof. The machine may operate as a standalone device or may be connected (e.g., networked) to other machines. While only a single machine is illustrated, the term "machine" shall also be taken to include any collection of machines that individually or jointly execute a set (or multiple sets) of instructions to perform any one or more of the methodologies discussed herein.

The machine-readable medium may include a single medium or multiple media (e.g., a centralized or distributed database, and/or associated caches and servers) that store the one or more instructions or data structures. The term "machine-readable storage medium" shall also be taken to include any tangible medium that is capable of storing, encoding or carrying instructions for execution by the machine and that cause the machine to perform any one or more of the methods of the present invention, or that is capable of storing, encoding or carrying data structures used by or associated with such instructions. The term "machine-readable storage medium" shall accordingly be taken to include, but not be limited to, solid-state memories, and optical and magnetic media. Specific examples of machine-readable media include non-volatile memory, including by way of example, semiconductor memory devices (e.g., erasable programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks. A "machine-readable storage medium" shall also include devices that may be interpreted as transitory, such as register memory, processor cache, and RAM, among others. The definitions provided herein of machine-readable medium and machine-readable storage medium are applicable even if the machine-readable medium is further characterized as being "non-transitory." For example, any addition of "non-transitory," such as non-transitory machine-readable storage medium, is intended to continue to encompass register memory, processor cache and RAM, among other memory devices.

In various examples, the instructions may further be transmitted or received over a communications network using a transmission medium. The instructions may be transmitted using the network interface device and any one of a number of well-known transfer protocols (e.g., HTTP). Examples of communication networks include a LAN, a WAN, the Internet, mobile telephone networks, plain old telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A system for determining a rotational orientation of a lead for use in electrostimulation of a body tissue, wherein the lead has a longitudinal axis and a marker configured to identify a rotational orientation about the longitudinal axis of the lead, the system comprising:
   a data input circuit configured to receive computed tomography (CT) image data of at least a portion of the lead including CT image data of the marker;
   a template receiver circuit configured to receive at least one template of the lead having a specified rotational orientation, the at least one template including (1) a reference data cube ($X_R$) of the marker and (2) a reference marker direction vector ($v_R$) indicative of the specified rotational orientation of the lead;
   a lead orientation estimator circuit, including:
      a marker recognition circuit configured to produce a target data cube ($X_T$) of the marker using the CT image data of the marker;
      a data registration circuit configured to register the reference data cube ($X_R$) to the target data cube ($X_T$) to produce a transformation operator ($\Phi$) for transforming $X_R$ into a transformed reference data cube $\Phi(X_R)$ that matches $X_T$ within a specified margin; and
      an estimator circuit configured to estimate the rotational orientation of the lead using the reference marker direction vector ($v_R$) and the determined transformation operator ($\Phi$);
   an output unit, configured to produce a graphical representation of the lead and the estimated rotational orientation of the lead.

2. The system of claim 1, wherein the marker recognition circuit is configured to identify the marker using an anisotropic shape of the CT image data of the marker, and produce the target data cube ($X_T$) of the marker using the CT image data of the identified marker.

3. The system of claim 2, wherein the marker includes a first portion and a second portion, the first portion including a radiopaque band around a circumference of the lead, the radiopaque band having an anisotropic shape of a bulge in the CT image data, and the second portion defining a radiolucent window having an anisotropic shape of a dimple in the CT image data.

4. The system of claim 1, further comprising a template formation circuit, coupled to the data input circuit, configured to generate a template of the lead, wherein:
   the data input circuit is configured to receive CT image data of the lead obtained when the lead is substantially aligned with an imaging axis, the CT image data including CT image data of the marker; and
   the template formation circuit is configured to:
      identify a lead tip and a lead shaft using the CT image data;
      detect a lead axis using the identified lead tip and lead shaft;
      identify the marker using the CT image data of the marker;
      produce the reference data cube ($X_R$) of the template using the CT image data of the marker and the detected lead axis; and
      determine the reference direction vector ($v_R$) of the template using the reference data cube.

5. The system of claim 4, wherein the template formation circuit is configured to determine the reference direction vector, including:
   detect a midpoint of the marker using the identified lead tip and the lead shaft;
   detect a bulging point within the identified marker, the bulging point being spatially farther away from the midpoint of the marker than other points within the identified marker;
   generate an initial marker direction vector that originates at the midpoint of the marker and points to the bulging point; and
   determine the reference direction vector ($v_R$) as a projection of the initial marker direction vector onto a plane perpendicular to the detected lead axis.

6. The system of claim 4, wherein the template formation circuit is configured to determine the reference direction vector, including:
   identify a symmetric plane through the detected lead axis around which the CT image data of the marker is substantially reflective symmetric;
   produce two candidate marker direction vectors along the symmetric plane, the two candidate marker direction vectors originating from and perpendicular to the lead axis, and pointing to two opposite directions; and determine the reference direction vector ($v_R$) as one of the two candidate marker direction vectors that is spatially closer to a bulging point within the identified marker than the other of the two candidate marker direction vectors.

7. The system of claim 1, wherein the lead orientation estimator circuit is configured to estimate the rotational orientation of the lead by applying the determined transformation operator ($\Phi$) to the reference direction vector ($v_R$) to produce an estimated marker direction vector ($\tilde{v}_T$) indicative of the rotational orientation of the lead relative to an imaging axis used for producing the CT image data of the at least a portion of the lead.

8. The system of claim 1, wherein:
the template receiver circuit is configured to receive two or more templates of the lead; and
the data registration circuit is configured to perform a multi-atlas registration of respective reference data cubes associated with the two or more templates to the target data cube.

9. The system of claim 8, wherein the estimator circuit is configured to:
produce two or more estimated marker direction vectors of the lead by applying the respective transformation operators to the reference direction vector ($v_R$); and
determine the rotational orientation of the lead using a combination of the two or more estimated marker direction vectors.

10. The system of claim 9, wherein the estimator circuit is configured to produce a confidence indicator of the estimated rotational orientation of the lead using the two or more estimated marker direction vectors.

11. The system of claim 10, further comprising an electrostimulator circuit configured to generate directional electrostimulation for modulating the body tissue using the lead oriented at least according to the estimated rotational orientation.

12. A system for determining a rotational orientation of a lead for use in electrostimulation of a body tissue, wherein the lead has a longitudinal lead axis and a marker configured to identify a rotational orientation about the longitudinal axis of the lead, the system comprising:
a data input circuit configured to receive image data of at least a portion of the lead including image data of the marker;
a template receiver circuit configured to receive at least one template of the lead having a specified rotational orientation, the at least one template including (1) a reference data cube ($X_R$) of the marker and (2) a reference marker direction vector ($v_R$) indicative of the specified rotational orientation of the lead;
a lead orientation estimator circuit, including:
a marker recognition circuit configured to produce a target data cube ($X_T$) of the marker using the image data of the marker;
a data registration circuit configured to register the reference data cube ($X_R$) to the target data cube ($X_T$) to produce a transformation operator ($\Phi$) for transforming $X_R$ into a transformed reference data cube $\Phi(X_R)$ that matches $X_T$ within a specified margin, wherein the transformation operator ($\Phi$) includes at least one non-rigid transformation to reduce local geometric discrepancies by aligning the reference data cube ($X_R$) with the target data cube ($X_T$); and an estimator circuit configured to estimate the rotational orientation of the lead using the reference marker direction vector ($v_R$) and the determined transformation operator ($\Phi$);
an output unit, configured to produce a graphical representation of the lead and the estimated rotational orientation of the lead.

13. The system of claim 12, wherein the data input circuit is configured to receive the image data including data of a computed tomography (CT) scan of the marker.

14. A method for determining a rotational orientation of a lead for use in electrostimulation of a body tissue, wherein the lead has a longitudinal axis and a marker configured to identify a rotational orientation about the longitudinal axis of the lead, the method comprising:
receiving computed tomography (CT) image data of at least a portion of the lead including CT image data of the marker;
receiving at least one template of the lead having a specified rotational orientation, the at least one template including (1) a reference data cube ($X_R$) of the marker and (2) a reference marker direction vector ($v_R$) indicative of the specified rotational orientation of the lead about the longitudinal axis;
producing a target data cube ($X_T$) of the marker using the CT image data of the marker;
registering the reference data cube ($X_R$) to the target data cube ($X_T$) to produce a transformation operator ($\Phi$) for transforming $X_R$ into a transformed reference data cube $\Phi(X_R)$ that matches $X_T$ within a specified margin; and
estimating the rotational orientation of the lead using the reference marker direction vector ($v_R$) and the determined transformation operator ($\Phi$).

15. The method of claim 14, wherein receiving the CT image data includes receiving CT image data of a computed tomography (CT) scan of the marker.

16. The method of claim 14, further comprising creating a template of the lead, including:
receiving CT image data of the lead obtained when the lead is substantially aligned with an imaging axis, the CT image data of the lead including CT image data of the marker;
identifying a lead tip and a lead shaft using the CT image data;
detecting a lead axis using the identified lead tip and lead shaft;
identifying the marker using the CT image data;
producing a reference data cube ($X_R$) of the template using the CT image data of the marker and the detected lead axis; and
determining a reference direction vector ($v_R$) of the template using the reference data cube.

17. The method of claim 16, wherein determining the reference direction vector includes:
detecting a midpoint of the marker using the identified lead tip and the lead shaft;
detecting a bulging point within the identified marker, the bulging point being spatially farther away from the midpoint of the marker than other points within the identified marker;
generating an initial marker direction vector that originates at the midpoint of the marker and points to the bulging point; and
determining the reference direction vector ($v_R$) as a projection of the initial marker direction vector onto a plane perpendicular to the detected lead axis.

18. The method of claim 16, wherein determining the reference direction vector includes:
    identifying a symmetric plane through the detected lead axis around which the CT image data of the marker is substantially reflective symmetric;
    producing two candidate marker direction vectors along the symmetric plane, the two candidate marker direction vectors originating from and perpendicular to the lead axis, and pointing to two opposite directions; and
    determining the reference direction vector ($v_R$) as one of the two candidate marker direction vectors that is spatially closer to a bulging point within the identified marker than the other of the two candidate marker direction vectors.

19. The method of claim 14, wherein estimating the rotational orientation of the lead includes applying the determined transformation operator ($\Phi$) to the reference direction vector ($v_R$) to produce an estimated marker direction vector ($\tilde{v}_T$) indicative of the rotational orientation of the lead relative to an imaging axis used for producing the CT image data of the at least a portion of the lead.

20. The method of claim 14, wherein:
    registering the reference data cube ($X_R$) to the target data cube ($X_T$) includes performing a multi-atlas registration of respective reference data cubes associated with two or more of the templates to the target data cube, to produce respective transformation operators corresponding to the two or more of the templates; and
    estimating the rotational orientation of the lead includes estimating the rotational orientation using a combination of the two or more estimated marker direction vectors estimated using reference direction vectors and respective transformation operators.

* * * * *